United States Patent [19]
Van Kersen et al.

[11] Patent Number: 5,948,397
[45] Date of Patent: Sep. 7, 1999

[54] SKIN CARE TREATMENT FOR EMBALMED BODIES

[75] Inventors: Chris Van Kersen, Troy; Ronald Fletcher, Dayton, both of Ohio

[73] Assignee: New Concept Marketing, Inc., Cincinnati, Ohio

[21] Appl. No.: 08/942,630

[22] Filed: Oct. 2, 1997

[51] Int. Cl.⁶ .............................. A01N 1/00; A61K 47/00
[52] U.S. Cl. ............................................ 424/75; 514/781
[58] Field of Search ................................ 424/75; 514/781

[56] References Cited

U.S. PATENT DOCUMENTS

| | | | |
|---|---|---|---|
| 4,263,278 | 4/1981 | Saurino et al. | 424/75 |
| 4,952,560 | 8/1990 | Kigasawa et al. | 514/2 |
| 5,516,808 | 5/1996 | Sawaya | 514/781 |
| 5,529,770 | 6/1996 | McKinzie et al. | 424/78.24 |
| 5,679,333 | 10/1997 | Dunphy | 424/75 |

*Primary Examiner*—William R. A. Jarvis
*Attorney, Agent, or Firm*—Wood, Herron & Evans LLP

[57] ABSTRACT

This is a two-part system to protect the skin of deceased individuals. It includes a moisturizing composition that provides both moisture and protein to the surface of the skin. After moisturization, a sealer composition is applied to prevent further moisture loss. The system restores the appearance of skin after an individual has died and preserves the appearance.

7 Claims, No Drawings

SKIN CARE TREATMENT FOR EMBALMED BODIES

BACKGROUND OF THE INVENTION

In order to preserve bodies for burial and other associated services, the body is frequently embalmed. This embalming preparation, although preventing significant deterioration of the body, does significantly dry out the body and in particular the skin. This, in turn, causes the skin to have an unnatural appearance. The protein in the skin is actually denatured. Since the tissue is no longer living, typical moisturizing creams used for living individuals will not function properly. However, without this moisturization the skin simply cannot take on a normal, natural appearance.

SUMMARY OF THE INVENTION

The present invention is premised upon the realization that the skin of embalmed bodies can be remoisturized by applying to the skin a moisturizing composition structurally related to the lipid stereochemistry of living tissue and subsequently sealing this with a wax-like matrix.

More particularly, the sealing composition of the present invention comprises a carrier such as carboxymethylcellulose, in combination with a water matrix such as methylmethacrylate gel, in combination with humectants, hydrolyzed protein and a liquid crystalline carrier. This, when applied to the skin, will cause moisture to migrate from the water matrix into the skin. Likewise, the hydrolyzed protein will, in turn, strengthen the skin and provide greater flexibility. The migration of the water and hydrolyzed protein is further facilitated by the addition of liquid crystalline material, in particular cholesteric esters. After application, this composition is sealed onto the skin by coating the skin with a hydrolipoid complex, related to an essential oil possessing tertiary realignment to the terminal end of the hydroxy group.

The objects and advantages of the present invention will be further appreciated in light of the following detailed description.

DETAILED DESCRIPTION

The present invention is an aqueous skin care composition for application to the skin of an embalmed body and a moisture barrier or sealant. The skin care composition includes a carrier, a water matrix composition, hydrolyzed protein, humectants, liquid crystals, and of course water.

The carrier is preferably an aqueous-based viscosity-increasing agent. The preferred composition is carboxymethylcellulose neutralized with triethanolamine to establish a viscosity of preferably about 250,000. The viscosity can vary ±50,000 or more. This simply builds viscosity in the composition. This should be present in an amount of 0.5 to about 1.5% by weight.

Water is provided in the system using a water matrix. This water matrix is a composition which will hold the water in suspension and allow it to migrate into the surface of the body. Preferably, the water matrix is a polyacrylate gel, preferably methylmethacrylate gel such as Lubrigel which is present in an amount from 0.25 to about 2.0% by weight.

In addition to the water matrix, the composition should include a source of hydrolyzed protein, either collagen or marine based protein. This acts to restore strength to the skin which has been dried out by the embalming fluid which denatures the protein in the skin. The protein also acts to retexturize the skin. This should be present in an amount of 0.5 to about 4.0% by weight.

Additionally, there should be one or more humectants. Many compositions act as humectants such as glycerin, polypropylene glycol, ethylene glycol and urea. Two commercially available humectants which are useful in the present invention are Petavatim and Hispagel. The humectant should be present in an amount from about 1% to about 10%. A mixture of different humectants can be employed if desired.

In addition to the humectants, there should be a liquid crystalline material, basically either a blue or a green cholesteric ester. This acts to carry the hydrolyzed protein into the skin. This should be present in an amount from about 1% to about 5%.

Finally, the remainder of the composition should be water. Other ingredients, such as polypropylene glycol, ethylene glycol, aloe and the like, can be included in the moisturizing composition to improve the appearance of the skin. One preferred formulation is as follows:

|  | Specific Formulation | Preferred Range (%) |
|---|---|---|
| Carbspel 940-910 (Carbopol ®) | 1% | 0.5–1.5 |
| Lubragel | 1% | 0.25–2.0 |
| Triethanol amine (TEA) | >1% | 0.1–1.0 |
| Hydrolyzed proteins | 2% | 0.5–4.0 |
| Glycerin | 1% | 0.25–3.0 |
| Polypropylene Glycol (PPG) | 0.8% | 0.1–2.0 |
| Aloe extract | 0.5% | 0.1–1.0 |
| Algae extract | 0.5% | 0.1–2.0 |
| Butylene glycol | 0.5% | 0.1–1.0 |
| Imidazolinyl urea | 0.5% | 0.01–1.5 |
| Petavatim (humectant) | 0.5% | 0.1–1.0 |
| Hispagel (humectant) | 1.0% | 0.5–1.0 |
| Germall (humectant) | 0.5% | 0.5–1.5 |
| Cholesteric esters, blue-green | 2–4% | 1.0–5.0 |
| Carbspel | 10% | 5.0–15.0 |

This composition is simply brushed of an individual and allowed to soak in for a period of time until the skin is not noticeably wet. This allows intracellular absorption and chemical rebuilding to take place. After rehydration, it is important to prevent further drying of the skin. Therefore, a sealer is applied. Basically, the sealer is a skin-compatible lipid barrier to moisture loss across the stratum corneum. The sealing composition includes a lipoid composition, a preservative and a bactericide. The lipoid composition preferably includes a glycol in combination with a gluconate gel carrier in combination with a hydroxypropylmethyl cellulose. Preferably, propylene glycol is employed as the glycol, and chlorhexidene gluconate as the gluconate. Preferably, the formulation will include 20–70% glycol, with about 47.25% preferred, 20–70% chlorhexidine gluconate (a gel-based carrier and antimicrobial) with 47.25% preferred, and 1–5% hydroxypropylmethyl cellulose with about 1.25% preferred, the remainder being water. Opadry, which is approximately a 50% solution of hydroxypropylmethyl cellulose, can be added in the amount of 1–10% as the hydroxypropylmethyl cellulose, with 2.5% being preferred.

The preservative, added in the amount of 1–10%, can be any number of preservatives such as ethanol, isopropyl alcohol, SDA-3, and SDA-4. The standard bactericides can be used in an amount from 0.5–2%. These can be, for example, Germall or methyl paraben. This sealing composition is simply blended together in the desired proportions to formulate the sealant composition. This is applied as an aqueous solution or emulsion which, upon drying, forms a thin, virtually unnoticeable film coating over the skin of the body, preventing moisture from escaping.

This has been tested on the skin of embalmed bodies and was found to effectively restore the appearance of the skin, making it appear to be the same as living tissue. Makeup can then be applied to the skin to restore color and the like.

Thus, the present invention provides a more life-like appearance.

This has been a description of this invention, but the invention should be defined by the appended claims wherein we claim:

1. A method of restoring skin of an embalmed body comprising applying to said skin a moisturizing composition effective to moisturize skin;
   wherein said moisturizing composition comprises a water matrix gel, water, hydrolyzed protein and cholesteric ester; and
   applying an aqueous based sealing composition onto said skin to prevent moisture added to said skin from evaporating.

2. The method claimed in claim 1 wherein said moisturizing composition further comprises a carrier and humectant.

3. The method claimed in claim 2 wherein said carrier is carboxymethyl cellulose.

4. The method claimed in claim 2 wherein said water matrix gel is a polyacrylate gel.

5. The method claimed in claim 4, wherein said polyacrylate gel is polymethylmethacrylate.

6. The method claimed in claim 2, wherein said humectant is selected from the group consisting of glycerin, propylene glycol, ethylene glycol, urea and combinations thereof.

7. The method claimed in claim 2 wherein said aqueous-based sealing composition comprises hydroxypropylmethyl cellulose.

* * * * *